United States Patent [19]

Joa

[11] 3,998,447
[45] Dec. 21, 1976

[54] METHOD AND APPARATUS FOR FOLDING FLAPS OF A SANITARY PAD

[76] Inventor: Curt G. Joa, P.O. Box 1121, Boynton Beach, Fla. 33435

[22] Filed: Sept. 4, 1975

[21] Appl. No.: 610,199

[52] U.S. Cl. .............................. 270/61 R; 270/68 R
[51] Int. Cl.² ........................................ B65H 45/00
[58] Field of Search ................. 270/61 R, 68 R, 69, 270/68 A, 86, 70; 93/84 R, 84 FF; 53/117, 387; 156/226–227

[56] References Cited
UNITED STATES PATENTS

| | | | |
|---|---|---|---|
| 1,682,237 | 8/1928 | Osborn | 270/68 R |
| 1,957,651 | 5/1934 | Joa | 93/84 R |
| 2,106,953 | 2/1938 | Ludewig | 270/69 |
| 3,116,668 | 1/1964 | Novick | 270/69 |
| 3,116,920 | 1/1964 | Geer | 270/70 |
| 3,447,987 | 6/1969 | Williams | 156/227 |
| 3,635,462 | 1/1972 | Joa | 270/86 |

*Primary Examiner*—Clifford D. Crowder
*Assistant Examiner*—A. Heinz
*Attorney, Agent, or Firm*—Joseph P. House, Jr.

[57] ABSTRACT

Method and apparatus for folding first and second end flaps of a sanitary pad, such as a disposable diaper, against the pad. The pad is advanced in one direction with the first flap disposed at the front end of the pad and the second flap disposed at the rear end of the pad. The first flap is allowed to drop into a conveyor gap and the conveyor wipes this flap over a folding element beyond the gap, thus to fold the first flap back against the pad. The pad is then turned end-for-end, desirably by conveying it around a vertical curve, thus to invert the pad and to dispose the second flap at the end of the pad which is now its front end with respect to said one direction. The second flap is now folded back against the pad desirably by advancing it again in said first direction and wiping it against a folding bar over which it is draped in the course of its inversion.

20 Claims, 6 Drawing Figures

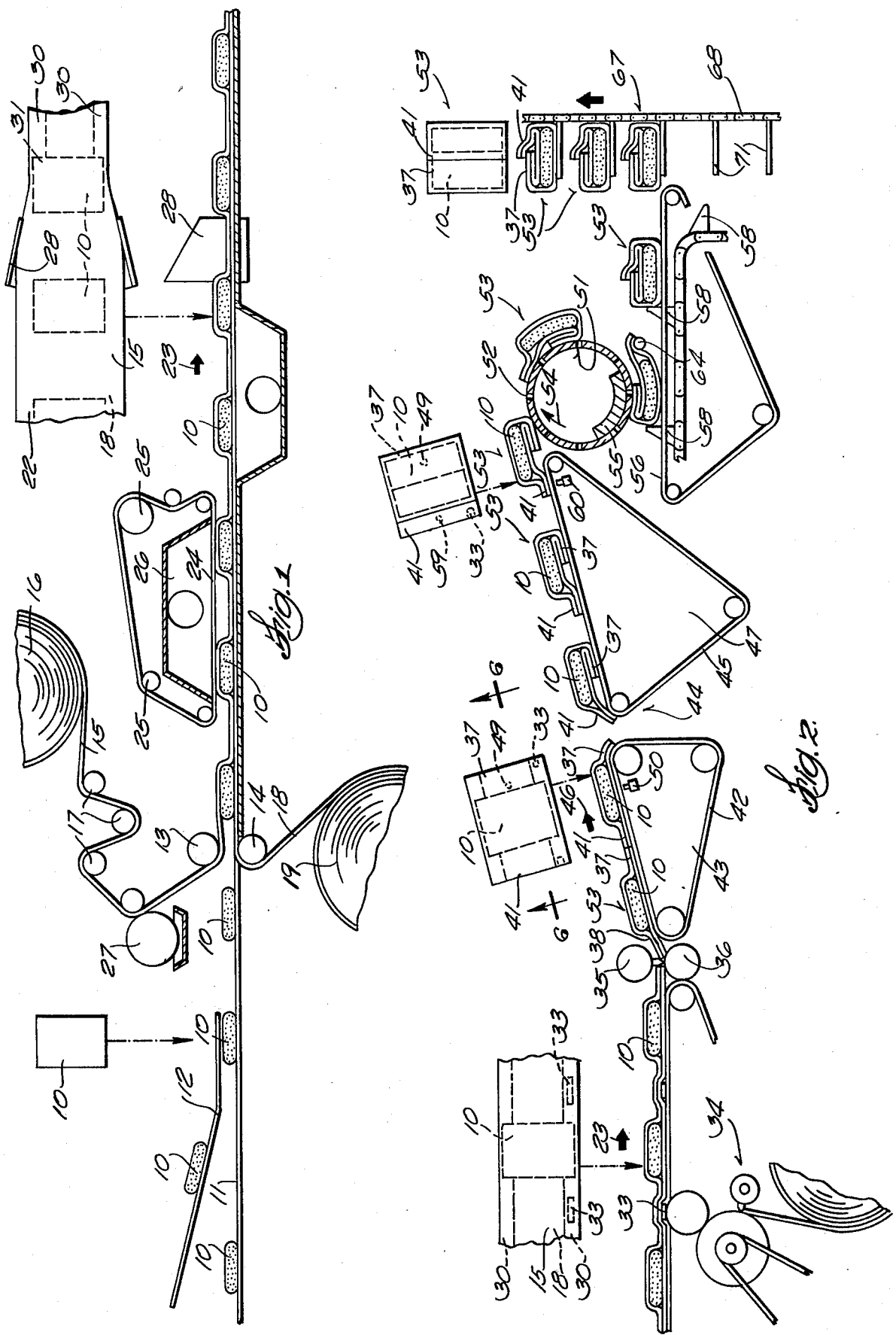

METHOD AND APPARATUS FOR FOLDING FLAPS OF A SANITARY PAD

BACKGROUND OF THE INVENTION

Copending U.S. Pat. application Ser. No. 524,852 filed Nov. 18, 1974 and now abandoned, shows a technique for folding first and second end flaps over the ends of a pad for a disposable diaper while the pad is continuously moving in one direction. The present invention has a similar objective, but utilizes a materially different technique. Part of this technique for folding one flap is based upon my U.S. Pat. No. 1,957,651 of May 8, 1934. However, I have greatly improved this technique in the present invention and utilize an entirely different technique for folding the other flap.

SUMMARY OF THE INVENTION

In accordance with the present invention, the first flap disposed at the front end of the pad is folded back against the pad while the pad is advanced in one direction. This desirably is accomplished in a manner similar to that shown in my prior U.S. Pat. No. 1,957,651 in which the flap drops into a gap between two conveyors and is folded back against the pad as the pad continues over the conveyor located beyond the gap. However, in the present invention, it is advantageous to vacuumize the belt which carries the pad to insure that the front flap will drop into the gap.

The second flap which is originally at the trailing end of the pad is now brought to the front of the advancing pad by turning the pad end-for-end so that this previously trailing flap is now the leading flap and can be wiped across a turning bar to fold it back against the pad and over the previously folded first flap. For this purpose, I invert the pad to turn it end-for-end. The technique utilized for inverting the pad desirably involves conveying it on a vertical curve so that near the end of its travel around the curve, it is moving against said one direction. However, as soon as the pad is inverted, it is dropped onto an underlying conveyor which is moving in said one direction and which picks up the inverted pad to move it again in said one direction and wipe it against the folding bar aforesaid.

Before making each fold, I desirably apply a glue spot in a position which will be embraced by the folded flap, thus to hold the flap is folded position. Moreover, the folded flap is desirably pressed against the pad and the intervening glue spot to enhance the bonding between the folded flap and the pad.

Other objects, features, and advantages of the invention will appear from the disclosure hereof.

DESCRIPTION OF THE DRAWINGS

FIG. 1 is a fragmentary schematic view illustrating a portion of the method and apparatus of the present invention in which discrete pad fillers are assembled with continuous top and bottom strips of an envelope for the pad filler. Strip portions between pad fillers constitute the flaps which are subsequently to be folded over the pad fillers. The apparatus is shown in side elevation and at appropriate locations I also illustrate the pad, strips, etc., in plan.

FIG. 2 is a fragmentary schematic view of a continuation of the illustration of FIG. 1 and showing one embodiment in which the strips between the pad fillers are cut off to define the first and second (leading and trailing) flaps and the technique for folding such flaps against the pad and transporting them to stacking mechanism. This embodiment utilizes a vacuum drum.

FIG. 6 is an enlarged cross section taken through a diaper before its end flaps are folded. This section is taken along the line 6—6 of FIG. 2.

DESCRIPTION OF THE PREFERRED EMBODIMENTS

Figure 3:
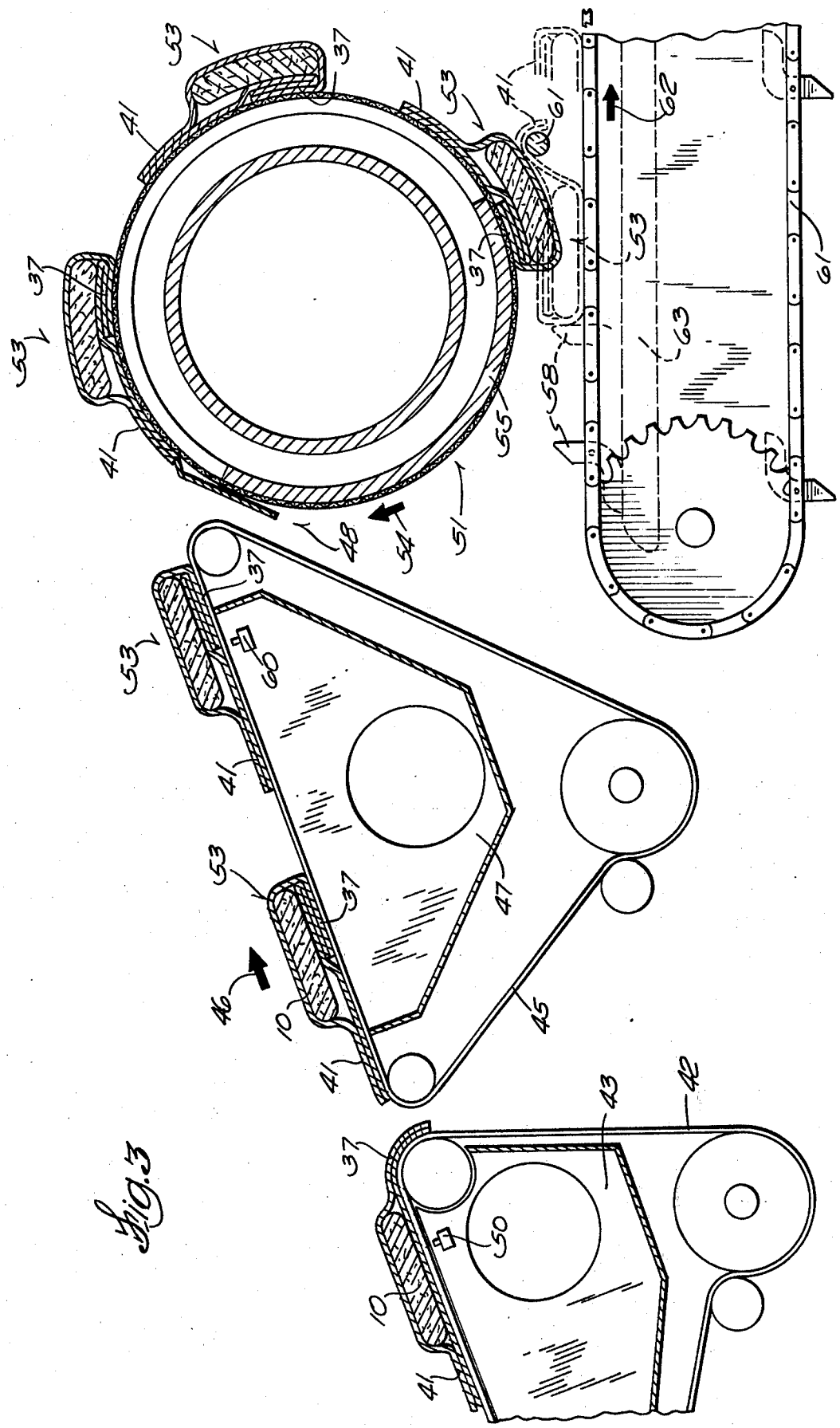
FIG. 3 is a schematic side elevation on an enlarged scale of that portion of the apparatus shown in FIG. 2 in which the flaps are folded against the pad.

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

FIG. 1 shows diagrammatically how discrete pad fillers 10 are advanced in staggered relation on separate vertically spaced belt conveyors 11, 12. All pads converge on belt 11 and are advanced in appropriately equally spaced relationship past upper roll 13 and lower roll 14. A web supply of plastic film strip 15 from parent roll 16 is fed over a series of intermediate rolls 17 and roll 13 to form the top strip of an envelope about the pads 10. A similarly dimensioned web strip 18 of non-woven tissue from parent roll 19 passes over the roll 14 to form the bottom envelope strip. The strips 15, 18 completely envelop the pads 10 and extend laterally therebeyond as indicated by the lateral margins 22 thereof, as is illustrated near the upper right-hand corner of FIG. 1.

Web 15 also passes over a patterned glue roll 27 which applies a diamond-shaped pattern of glue to that surface of the plastic web 15 which ultimately engages the pad 10 and the upper surface of the non-woven tissue web 18, thus to anchor the parts in assembled relation.

The conveyor 11 continues to move in the direction of arrow 23 and carries the assembly of strips 16, 18 and enveloped pad fillers 10 below a foraminous compression belt 24 which is trained over a series of rollers 25 and over a vacuum box 26.

The envelope margins 22 are folded over the sides of pad filler 10 by plows 28, thus to form cuffs 30 around the lateral margins 31 of pads 10, as shown at the upper right of FIG. 1.

The pad assembly continues to be conveyed in the direction of arrow 23 in FIG. 2 and adhesive tapes 33 are applied at spaced intervals to the undersurface of one of the folded cuffs 30 as shown at the upper left of FIG. 2 and midway between the longitudinally spaced pads 10 by tape applying apparatus 34 which is not part of the present invention, but which could be according to U.S. Pat. No. 3,772,120 of Nov. 13, 1973.

After the tapes 33 are applied, the pad assembly passes between a knife roll 35 and anvil roll 36 of a cutoff mechanism which completely severs through the assembly at cut line 41 midway between the encased pad fillers 10, thus to produce discrete pad segments 53 with laminated plastic and non-woven fabric strip panels extending fore and aft. The forwardly extending laminated panel is denominated a leading or first flap 37 and the rearwardly extending laminated panel is denominated a trailing or second flap 38.

After severance, the discrete pad segments 53 are passed over a vacuum belt 42 which travels over a vacuum box 43. The belt is foraminous, thus to hold the severed pad segments 53 in proper orientation, even though one pad segment 53 has been severed from the next.

At some convenient point before the flap 37 is folded, a spot of glue 49 is applied to flap 37 at its undersurface, approximately midway of its width and near the pad 10 (see FIG. 2). This is accomplished by glue jet 50.

The first or leading flap 37 is drawn by vacuum belt 42 downwardly into a gap 44 between vacuum belt 42 and another vacuum belt 45 which is spaced along the path of travel of the pad segments 53 in the direction of arrow 46. The pad body 10 continues to travel on the path of arrow 46 to bridge the gap and is picked up on the next foraminous belt 45 which travels over a vacuum box 47. In the course of moving across the gap 44, the first or leading flap 37 is folded back against the pad filler 10 and therebeneath as indicated in FIG. 2. Accordingly, as the discrete pad segments 53 continue on vacuum belt 45, there is a material space between successive pad segments 53 and in which the first or leading flap 37 has been folded beneath the pad filler 10 and the second or trailing flap 41 still extends rearwardly therefrom. The glue spot 49 bonds the flap 37 to the pad body 10 in the area thereof.

At some convenient point before the flap 41 is folded, a spot of glue 59 is applied to flap 41 at its underside, approximately midway of its width and near the pad 10. This is accomplished by a glue jet 60. The position of glue jets 59, 60 is not critical, as long as they apply glue spots before the flaps are folded.

The technique for folding the second or trailing flap 41 against the pad 10 and over a portion of the previously folded first flap 37 is also illustrated in FIG. 2 in which the pad segment 53 is transferred over gap 48 onto a pad carrier comprising a vacuum drum 51 which has a foraminous surface including a plurality of holes 52 exposed to the vacuum within the drum 51. The vacuum holds the pad segment 53 onto the drum 51 as illustrated in FIGS. 2 and 3. Drum 51 has its outer surface disposed on a vertical curve so that as the drum 51 rotates in the direction of arrow 54, the pad segment 53 near the bottom of its travel on the drum 51 will be moving in a direction opposite to arrow 46.

The glue spots 49 and vacuum drum 51 are examples of suitable means for holding the first flap 37 against the pad 10 while the pad is being turned end-for-end.

There is a slidable vacuum cutoff shutter 55 within the drum 51 so that when the pad segment 53 reaches its bottom-most position shown in FIGS. 2 and 3, it will drop off of the drum and onto a table 56 which has longitudinally extending slots 57 (FIG. 5) through which lugs 58 of paired lug conveyor chains 61 extend. The lugs 58 travel in the direction of arrow 62. The conveyor chains 61 advance the lugs 58 over a guide track 63 as in the construction shown in my U.S. Pat. No. 2,324,930 of July 20, 1943.

A folding bar 64 extends transversely over the table 56 and functions to wipe the second flap 41 over the pad filler 10 of the pad segment 53 as illustrated in FIGS. 2 and 3. Note that the shutter 55 in the vacuum drum 51 desirably has its leading edge 65 at a point where the bulk of the pad segment 53 will be dropped onto the table 56 in advance of lugs 58 and to the left of the folding bar 64 as shown in FIG. 3. The second flap 41 is still adhered to the drum as the body 10 is dropped onto the table 56 and continued movement of the drum in the direction of arrow 54 could carry the second flap 41 over the top of the pad body 10. However, this is not relied upon to complete the folding of the second flap 41.

I prefer to rely upon the folding bar 64 for this purpose as the second flap 41 may be stripped off of the drum 51 and be draped thereover as illustrated in FIG. 3. In any event, the conveyor chains 61 and lugs 58 will advance the pad segments 53 in the direction of arrow 62 in FIG. 3, thus wiping the second flap 41 against the turning bar 64 to fold the second flap 41 over the top of the pad body 10 and in overlapping relationship to the previously folded first flap 37.

By reason of the technique illustrated in FIGS. 2 and 3, in which the pad segment 53 is conveyed around the vacuum drum 51, the pad segment 53 is turned end-for-end with respect to its original movement in the direction of arrow 46. Accordingly, the second flap 41 which originally trailed the pad segment 53 is now at the front or leading edge of the pad segment 53 when the pad is picked up by the conveyor lugs 58. Accordingly, the folding of the two flaps 37 and 41 both occur while the pad segment 53 is being conveyed in the forward direction. This eliminates any need for backtracking and complicated mechanism for changing the direction of pad movement and yet has the decided advantage of folding both flaps 37, 41 while they are the leading flaps with respect to the direction of pad movement at the time folding occurs.

Figure 5:
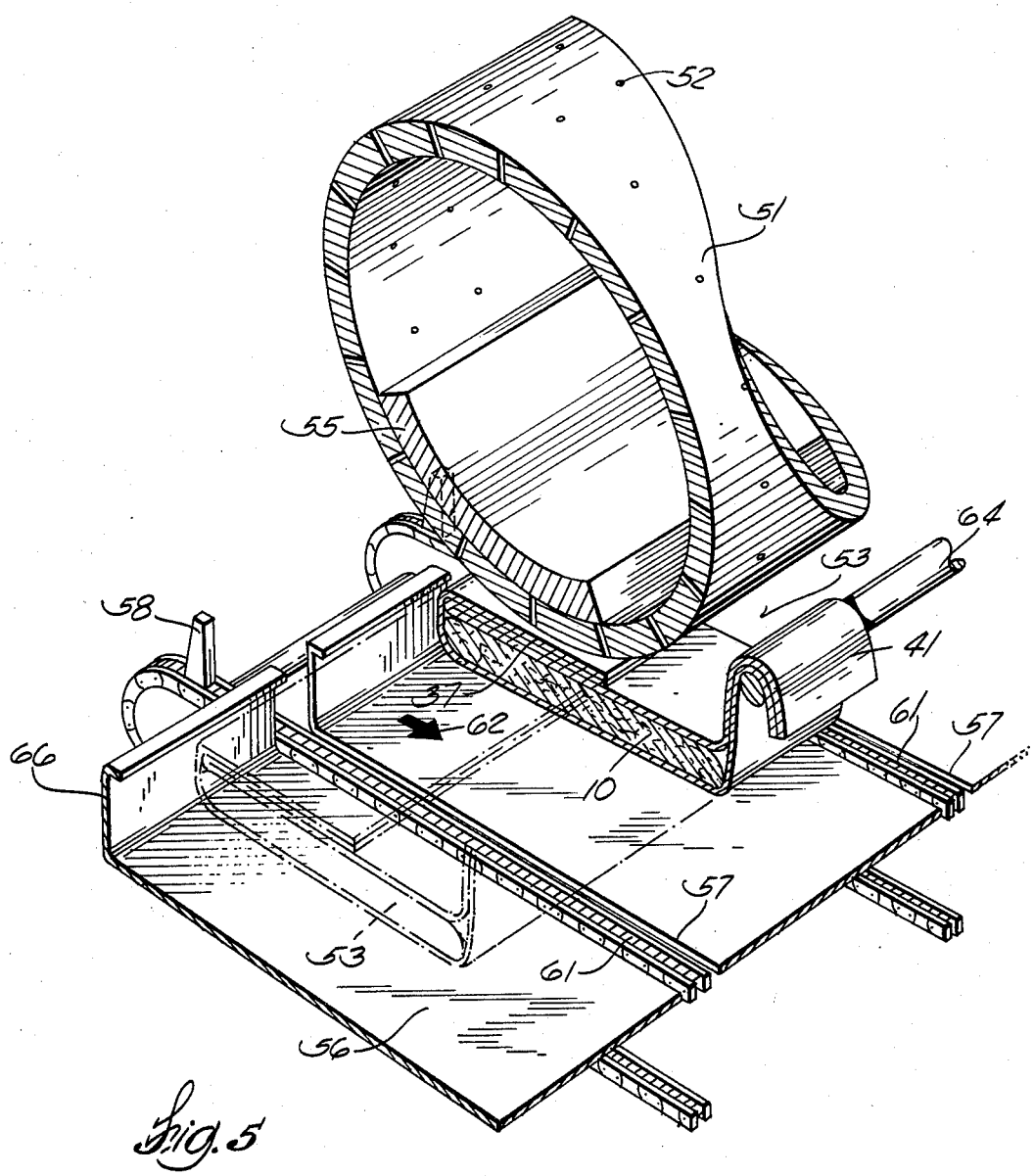
FIG. 5 is a fragmentary and somewhat diagrammatic perspective view of a modified embodiment of the structure shown in FIG. 3 and by which the second flap is folded against the pad.

FIG. 5 illustrates a modification in which the table 56 has its rear edge turned up to form a tray rail 66, thus insuring against the pad segment 53 being thrown rearwardly off of the table 56 because of any impetus imparted thereto by the rotation of drum 51. The slots 57 in table 56 are carried through into the rail 66 as illustrated in FIG. 5. In most installations, this rail 66 is not necessary as the lugs 58 of the chain conveyor 61 are typically in position to intercept the pad segment 53 when it leaves the drum 51 and is deposited thereby on table 56.

The completely folded pad segment 53 is now transported across the table 56, or is transferred to a belt and thence into a stacker 67 which has a chain conveyor 68 with a series of platforms or paddles 71, as is also illustrated in my U.S. Pat. No. 2,324,930 of July 20, 1943. The completely folded pad segment 53 is illustrated at the upper righthand corner of FIG. 2.

Figure 4:
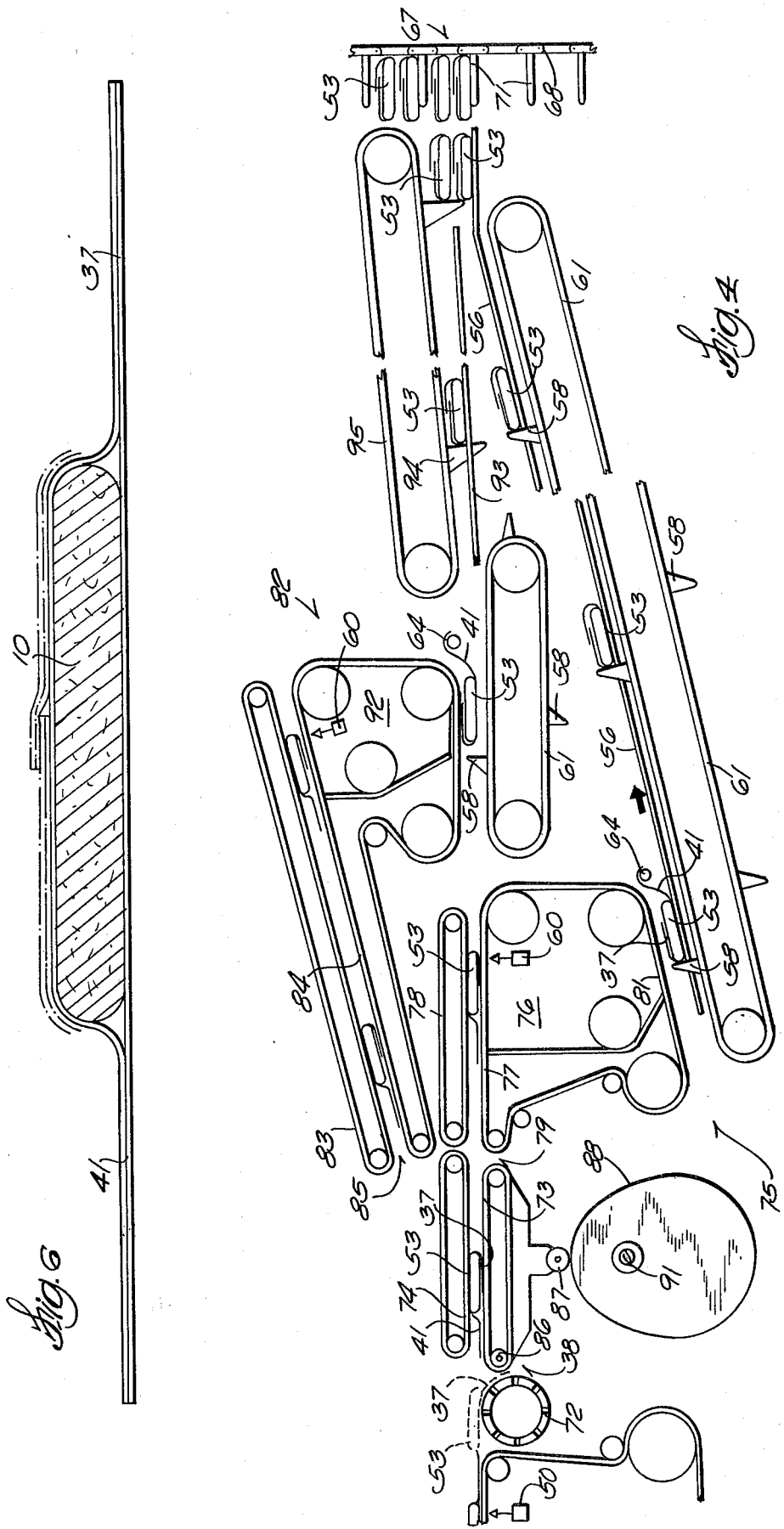
FIG. 4 is a schematic side elevation similar to FIG. 3, but showing a modified embodiment in which vacuum belts are used instead of the vacuum drum shown in FIG. 3.

FIG. 4 illustrates a modified embodiment in which the drum 51 of FIGS. 2, 3 and 5 is replaced by a pad carrier comprising formainous vacuum belts and in which the belts are double decked to increase production. In this embodiment, all of the apparatus up to the cutoff knife 35 and anvil roller 36 is substantially the same, as hereinbefore described. After cutoff, the discrete pad segment 53 is received by a vacuum roller or drum 72 which draws the first flap 37 down into a gap 38 just ahead of paired compression belts 73, 74. These complete the folding of first flap 37, substantially as hereinbefore described, and apply vertical pressure to the partially folded pad, as illustrated in FIG. 4. Following the paired compression belts 73, 74 there are double-decked sets of vacuum belts which respectively perform a folding function similar to the vacuum drum 51 of the previously described embodiment.

The lowermost vacuum belt assembly 75 comprises a vacuum box 76 over which foraminous vacuum belt 77 travels. Thereabove is a compression belt 78. Paired belts 77, 78 have a mouth 79 to receive pad segments 53 from belts 73, 74 and feed the pad segment 53 from left to right, as shown in FIG. 4, and around the curved path of belt 77. At the bottom of the vacuum box 76 there is a shiftable vacuum plate shutter 81 which cuts off vacuum to the pad segment 53 and drops the pad segment 53 onto a table 56 which is slotted in the same manner as the similar table shown in FIGS. 2, 3 and 5. Paired conveyor chains 61 having lugs 58 as hereinbefore described will advance the pad segments 53 past a folding bar 64, as hereinbefore described, to fold the second flap 41 against the pad 10 and over the previously folded flap 37.

There is a second flap folding mechanism 82 above the flap folder 75 and which is of substantially the same construction. The flap folding mechanism 82 has intake belts 83, 84 with an inlet mouth 85 at a higher elevation than the inlet mouth of the belts 77, 78 of the lower flap folding mechanism 75.

The previously described conveyors 73, 74 are mounted to swing on the axis 86 of the roller about which the lowermost belt 73 is trained and the entire structure is supported on a cam follower 87 which follows a contour of lift cam 88 which rotates on a shaft 91. Cam 88 is timed to swing the belt assembly 73, 74 vertically to alternately feed pad segments 53 into the mouth 79 of the lower folder assembly 75 and the mouth 85 of the upper folder assembly 82.

The foraminous belt 84 of upper folder assembly 82 passes about a vacuum box 92 having the same structure as the vacuum box 76 and which deposits pad segments 53 in advance of the lugs 58 of conveyor chains 61, as hereinbefore described. Lugs 58 will advance the pad segments 53 beneath a folding bar 64 to fold the second flap 41 over the top of the pad body 10.

As in the embodiment of FIGS. 1–3 and 5, the embodiment of FIG. 4 is provided with glue jets 50, 60 to apply glue spots to the flaps 37, 41 before they are folded.

Pads advanced by the conveyor chains 61 of the upper folder assembly 82 will be fed onto a table 93 and will be advanced by lugs 94 of the overhead chain conveyor 95. The lower conveyor chains 61 and the overhead chain conveyor 95 are coordinated so that two pad segments 53 will arrive together at the output end of the apparatus, as shown in FIG. 4, so that two such pad segments 53 will be stacked one on top of the other and will be received on the paddles 71 of stacker 67, as described in connection with FIG. 2.

In all of the embodiments hereinbefore described, suitable adjustments (not shown) are provided for positioning the folding bar 64 in proper relationship to the table 56, vacuum drum 51 and vacuum boxes 76, 92, depending upon the size of the diaper being processed thereon, the speed of the belts, chain conveyors, etc. Folding bar 64 is typically made of round bar stock, but can also assume other configurations, such as a flat strip, etc.

The thickness of the plies of the pad enclosure and end flaps 37, 41 is greatly exaggerated, for clarity in presentation, in FIGS. 1, 2, 3 and 5 of the drawings. The relative thickness of pad body 10 and end flaps 37, 41 is more accurately shown in FIG. 6, although the thickness of end flaps 37, 41 is exaggerated even in this figure.

What is claimed is:
1. The method of folding against a relatively thick pad first and second relatively thin flaps respectively at leading and trailing ends of said pad and comprising the steps of:
    advancing the pad in one direction with said first flap disposed at the leading end of the pad as it moves in said one direction and the second flap disposed at the trailing end of the pad as it moves in said one direction,
    folding said first flap back against the pad while advancing the pad in said one direction and while said first flap is at the leading end of the pad,
    turning the pad end-for-end before the second flap is folded against the pad, thus to dispose the second flap in its unfolded condition at the end of the pad which is now its leading end with respect to said one direction,
    holding the first flap against the pad while the pad is being turned,
    advancing the pad in said one direction, and
    folding said second flap back against the pad in the course of said advance and while the second flap is at the leading end of the pad.
2. The method of claim 1 in which the second flap is folded back against the pad by advancing the pad past a folding bar which wipes the second flap back against the pad.
3. The method of claim 2 in which the pad is advanced past the folding bar by pushing it with a chain-driven lug conveyor.
4. The method of claim 1 in which the advance of the pad in said one direction carries it over a gap, said first flap being folded back against the pad by dropping it into said gap and advancing the pad over the gap and wiping the first flap across a folding element beyond the gap.
5. The method of claim 1 in which the pad is turned end-for-end by conveying it around a vertical curve to invert the pad and start it moving in a direction opposite said one direction.
6. The method of claim 5 in which the pad is advanced in said one direction after it has been inverted.
7. The method of claim 5 in which vacuum is applied to said vertical curve to hold the pad thereto as it is inverted.
8. The method of claim 7 in which the vertical curve comprises a rotary vacuum drum.
9. The method of claim 7 in which the vertical curve comprises a vacuum belt.
10. Apparatus for folding against a relatively thick pad first and second relatively thin flaps respectively at leading and trailing ends of said pad and comprising:
    means for advancing the pad in one direction with said first flap disposed at the leading end of the pad as it moves in said one direction and said second flap at the trailing end of the pad as it moves in said one direction,
    means for folding said first flap back against the pad while advancing the pad in said one direction and while said first flap is at the leading end of the pad,
    means for turning the pad end-for-end before the second flap is folded against the pad, thus to dispose the second flap in its unfolded condition at the end of the pad which is now its leading end with respect to said one direction, means for holding the first flap against said pad while the pad is being turned, means for advancing the pad in said one direction, and means for folding said second flap back against the pad in the course of said advance and while the second flap is at the leading end of the pad.

11. The apparatus of claim 10 in which the means for folding the second flap back against the pad comprises a folding bar ahead of said flap and past which the second flap is wiped in the course of its advance.

12. The apparatus of claim 11 in which the means to advance the pad to wipe it against said folding bar comprises a chain-driven lug conveyor.

13. The apparatus of claim 10 in which the means for folding the first flap back against the pad comprises conveyor means having a gap below the pad and into which said flap will fall in the course of its advance, and a folding element beyond the gap to wipe said first flap against the pad as it is conveyed thereover by said conveying means.

14. The apparatus of claim 10 in which the means for turning the pad end-for-end comprises a conveyor having a vertical curve over which the pad is transported and of sufficient arcuate extent to invert the pad and start it moving in a direction opposite said one direction.

15. The apparatus of claim 14 in which the said means for advancing the pad after both said flaps have been folded thereagainst comprises means for engaging said pad after it has been inverted.

16. The apparatus of claim 14 in which there is a tray which catches the pad after it has negotiated the said vertical curve.

17. The apparatus of claim 16 in which said tray has slots and a lugged conveyor disposed in said slots.

18. The apparatus of claim 14 in which the conveyor having a vertical curve comprises a vacuum surface which will adhere the pad thereto in the course of its inversion.

19. The apparatus of claim 18 in which the vacuum surface comprises a foraminous drum.

20. The apparatus of claim 18 in which the vacuum surface comprises a foraminous belt.

* * * * *